United States Patent
Stirling et al.

(10) Patent No.: US 6,191,424 B1
(45) Date of Patent: Feb. 20, 2001

(54) IRRADIATION APPARATUS FOR PRODUCTION LINE USE

(75) Inventors: Andrew J. Stirling, Kanata; Gerald E. Hare, Nepean, both of (CA)

(73) Assignee: I-AX Technologies, Kanata (CA)

( * ) Notice: Under 35 U.S.C. 154(b), the term of this patent shall be extended for 0 days.

(21) Appl. No.: 09/204,262

(22) Filed: Dec. 3, 1998

(51) Int. Cl.⁷ .............................. H01J 37/30; G21K 1/04
(52) U.S. Cl. .............................. 250/455.11; 250/453.11; 250/492.3; 250/496.1
(58) Field of Search .................. 250/453.11, 455.11, 250/492.2, 492.3, 496.1

(56) References Cited

U.S. PATENT DOCUMENTS

| | | | |
|---|---|---|---|
| 3,225,203 | 12/1965 | Gombert | 250/106 |
| 3,433,947 | 3/1969 | Emanuelson et al. | 250/19.5 |
| 3,496,362 | 2/1970 | Kirkpatrick et al. | 250/106 |
| 4,866,281 | 9/1989 | Bosshard | 250/453.1 |
| 5,009,654 | 4/1991 | Minshall | 604/410 |
| 5,396,074 | * 3/1995 | Peck et al. | 250/453.11 |
| 5,401,973 | 3/1995 | McKeown et al. | 250/492.3 |
| 5,554,856 | 9/1996 | Bidnyy | 250/455.11 |
| 5,557,109 | 9/1996 | Bidnyy | 250/455.11 |
| 5,597,597 | * 1/1997 | Newman | 426/248 |
| 5,958,336 | * 9/1999 | Duarte | 422/24 |
| 5,994,706 | * 11/1999 | Allen et al. | 250/454.11 |

FOREIGN PATENT DOCUMENTS

| | | | | |
|---|---|---|---|---|
| 1 078 431 | 4/1964 | (GB) | ............... | G21H/5/00 |
| 1 078 963 | 3/1965 | (GB) | ............... | G21H/5/00 |
| 1 072 074 | 5/1965 | (GB) | ............... | G21H/5/00 |
| 1 263 638 | 6/1970 | (GB) | ............... | G21H/5/00 |
| 1 505 284 | 9/1975 | (GB) | ............... | C04B/7/36 |
| 87/05738 A1 | 9/1987 | (WO) | ............... | G21K/5/02 |

* cited by examiner

Primary Examiner—Bruce C. Anderson
Assistant Examiner—Nikita Wells
(74) Attorney, Agent, or Firm—Pascal & Associates (57) ABSTRACT

A production line irradiation apparatus used to sterilize medical equipment, food or agricultural and waste materials. The apparatus is compact in size and allows a continuous throughput of products to be irradiated, while preventing harmful radiation from escaping. The apparatus comprises: primary shield means for blocking radiation; secondary shield means for blocking radiation; an irradiation device; and conveyor means. The primary shield means further includes a central cavity therein and a channel extending therethrough which intersects the cavity and accommodates the conveyor means. The secondary shield means comprises a plurality of discrete open containers, the containers having front and rear walls, the walls being substantially the size of the channel opening. The walls of the primary and secondary shield means are of sufficient density to fully attenuate the radiation produced by the irradiation device. The containers are integral to the conveyor means and the irradiation device is disposed within the cavity to allow radiation of a product positioned in the containers as the containers pass through the cavity.

10 Claims, 10 Drawing Sheets

PRIOR ART

PRIOR ART

IRRADIATION APPARATUS FOR PRODUCTION LINE USE

FIELD OF INVENTION

This invention relates to irradiation equipment and in particular to compact, production-line sterilization equipment.

DESCRIPTION OF THE RELATED PRIOR ART

Manufacturers of sterile medical devices frequently use ionizing radiation to reduce the bioburden. Such radiation processing methods are also used for sterilizing, or rendering less harmful, other products such as foods, agricultural and waste materials and for crosslinking or scissioning polymers. Radiation may also be used for altering the physical properties of materials. Radiation sources for sterilization, scissioning and crosslinking typically include radioisotopes such as cobalt −60 or cesium 137, electron beam accelerators of energy greater than 1 MeV, or electron beam accelerators with heavy metal targets that convert the electrons into x-rays.

Typically, radiation processing is carried out after production and packaging of the product to be sterilized, at large sterilization plants, often located a considerable distance from the point of product manufacture. These high volume sterilization plants are expensive to build and very large in size, due to the thick radiation shielding and the need for a tortuous product transport path to prevent radiation leakage. In order to be cost-effective, this method of sterilization is generally used where a large volume of product is to be processed. As well, due to their size they cannot easily be integrated into the manufacturer's production line. Further, since these large capacity plants are often operated by independent service providing companies, a quality control system extending across more than one company is required. In addition, there can be a mixture of products processed at a given sterilization plant, which frequently results in the transfer from one product to another of undesirable characteristics such as odour.

Figure 1:
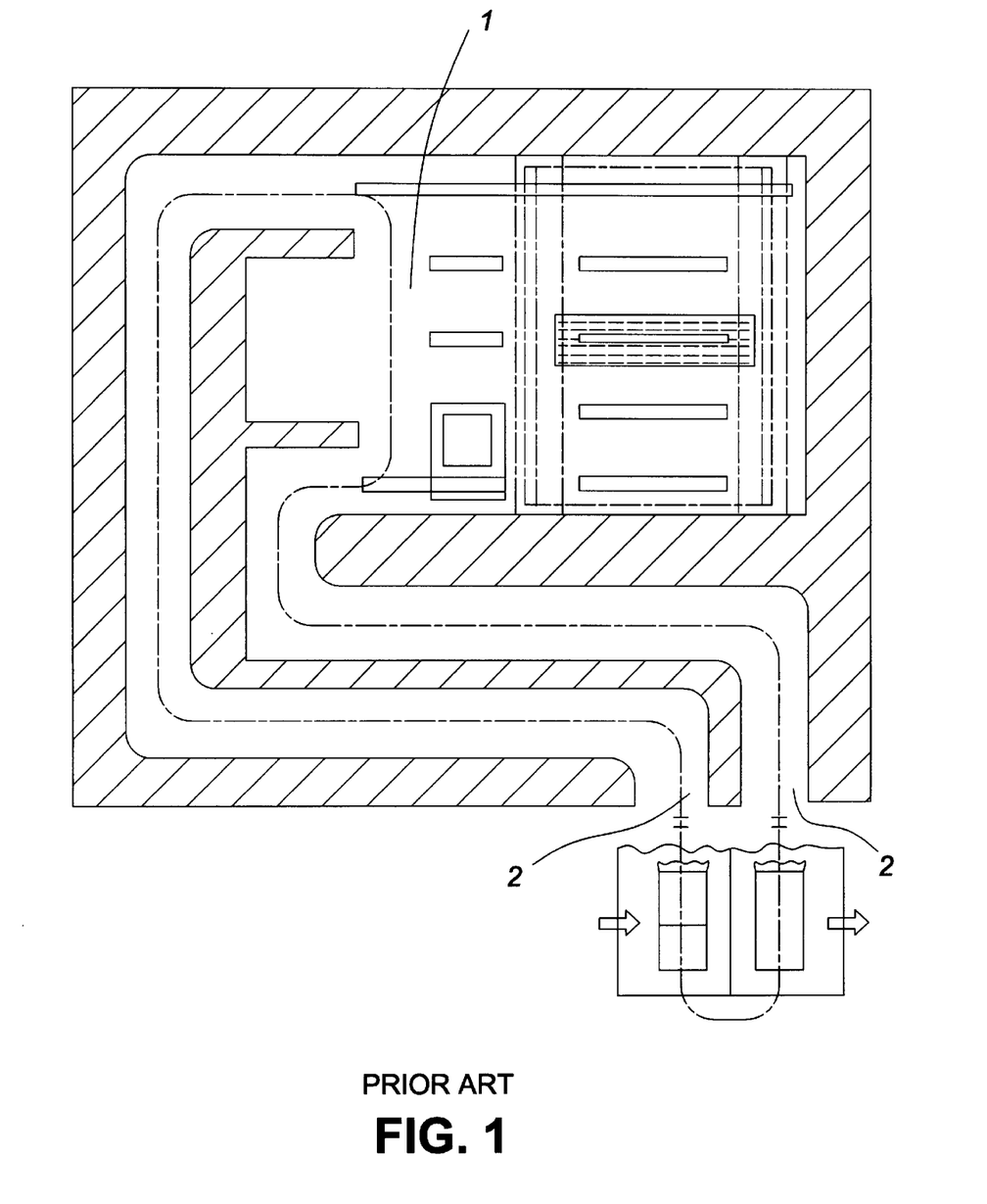
FIG. 1 is a top cut-away view of a first irradiation apparatus in accordance with the prior art.

An example of a typical large volume irradiator is described in U.S. Pat. No. 4,866,281 issued Sep. 12, 1989 and depicted in FIG. 1. In this unit, the attenuation of the radiation which can escape along the product path is eliminated by the use of a maze structure extending between the radiation zone 1 and the product entry/exit point 2. The size and complexity of the shield is therefore much larger than necessary to simply enclose the irradiation source and the product being irradiated.

Figure 2:
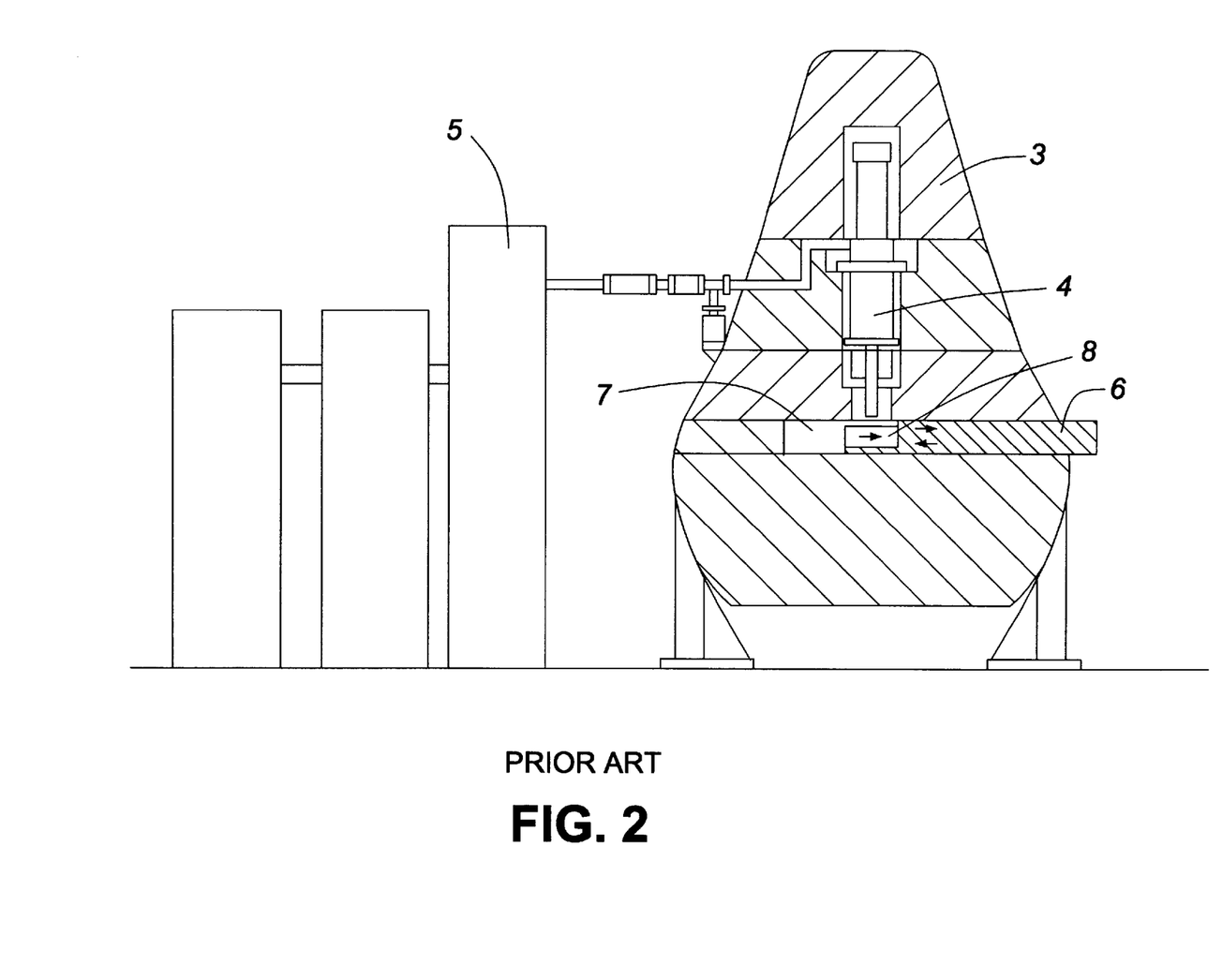
FIG. 2 is a side cut-away view of a second irradiation apparatus in accordance with the prior art.

In response to the demand for physically smaller systems, devices such as the one described in U.S. Pat. No. 5,557,109 issued Sep. 10, 1996 and shown as FIG. 2, were proposed. This system comprises a shielding unit 3, an irradiation device 4, a power supply, high frequency generator and modulator 5, and a manipulator 6. Products to be irradiated are placed in chamber 8 integral to manipulator 6 and the manipulator 6 is linearly received into the cavity 7 of shield 3, so that the product to be sterilized is aligned with the irradiation device 4. The related invention disclosed in U.S. Pat. No. 5,554,856 issued Sep. 17, 1996 uses a manipulator which can be rotated instead of linearly moved to place the product to be sterilized into the irradiation zone. While these devices do overcome the problem of size associated with earlier systems, they do not provide for a steady and continuous flow goods to be irradiated. These devices provide sequential rather than continuous processing, requiring labour and time-intensive product handling and the movement of a significant mass of the primary shield is necessary for the treatment of each unit processed. In the linear system for example, chamber 8 is accessed by moving the manipulator 6 which is constructed of a large slug of very dense and heavy shielding. Similarily, in the rotatable system, the manipulator is constructed from a large slug of shielding and has two chambers that must be loaded with product and rotated into the irradiation zone. The movement of the manipulator in both cases requires the acceleration and deceleration of a large mass of shielding, making neither system suitable for production line operations where higher throughput is required.

Figure 3:
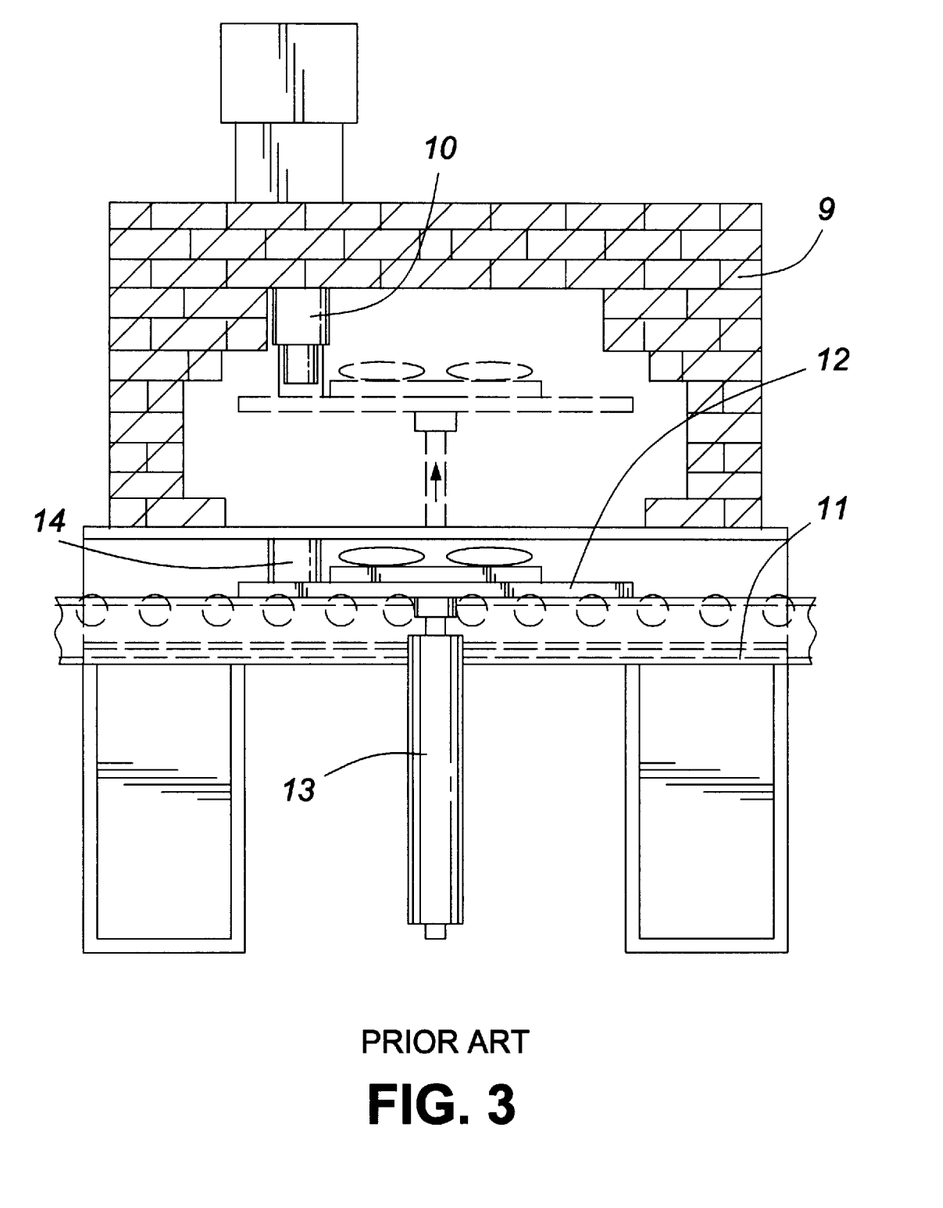
FIG. 3 is a side cut-away view of a third irradiation apparatus in accordance with the prior art.

U.S. Pat. No. 5,009,654 issued Apr. 23, 1991 and shown in FIG. 3, discloses another sequential production line system whose primary purpose is to irradiate one part of an assembly while shielding other radiation sensitive parts. The essential components of this system include a shielding unit 9, an irradiation device 10, a conveyor system 11, a carrier 12, a piston cylinder 13 and an isolation fixture 14. This system is designed to allow irradiation of a selected portion of a product to be irradiated by incorporating an isolation fixture 14 which comprises additional shielding to isolate the portion of the product to be irradiated. In operation, the carrier 12 is aligned with the piston cylinder 13 and the carrier 12 is lifted toward the irradiation device 10. The isolation fixture 14 integral to carrier 12 is placed directly in line with the irradiation device, facilitating sterilization of a selected portion of the product. Although this system satisfactorily provides localized sterilization, it is not a general product ion line sterilization system which can accommodate continuous product throughput. The use of a piston cylinder 13 to physically lift the carrier 12 is necessary to ensure that only a selected portion of the product is sterilized and to ensure that any radiation produced is attenuated by the shielding unit 9. However, lifting of the product unduly complicates the system and serves to reduce the volume of product which can be moved through the system.

Figure 4:
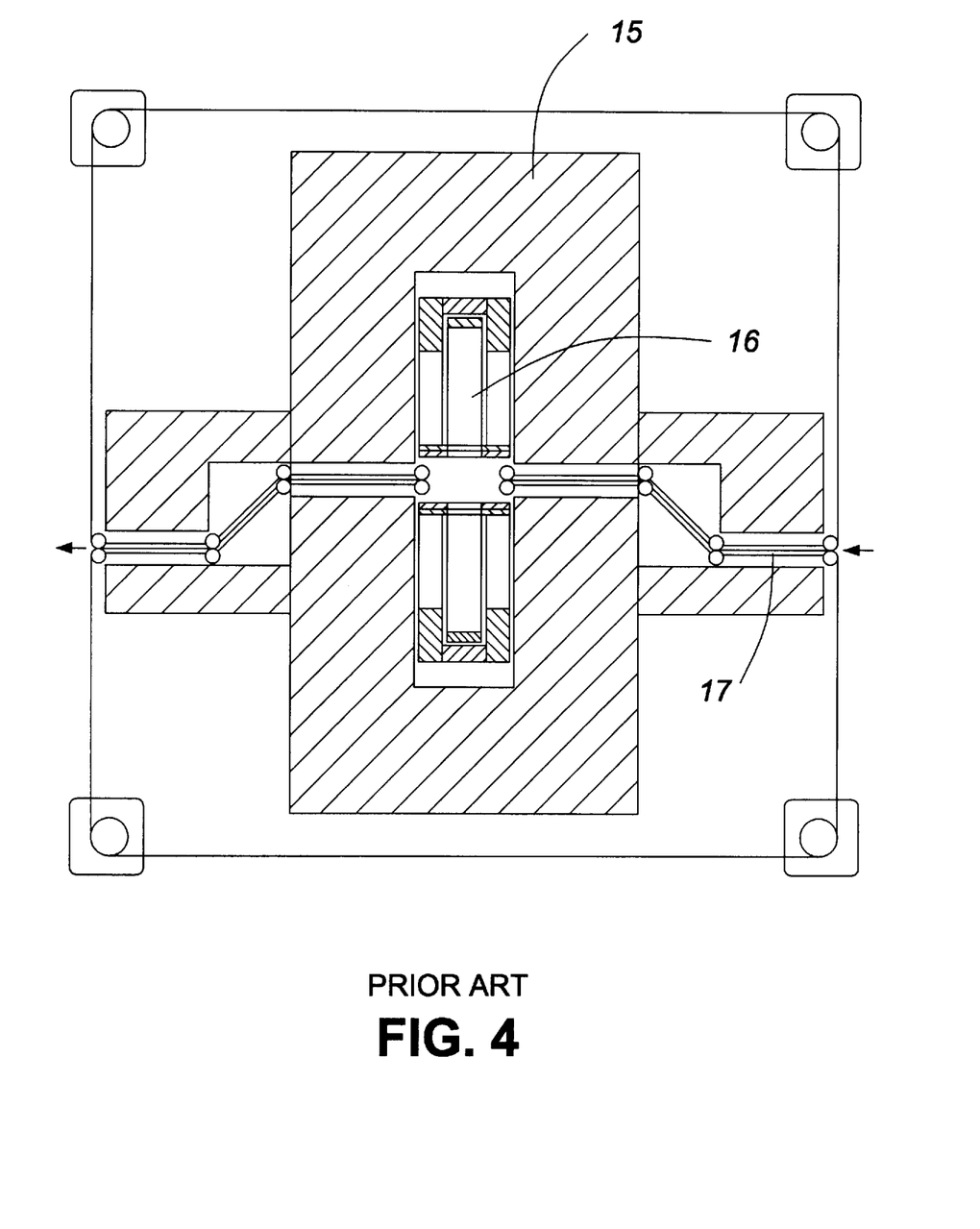
FIG. 4 is a side cut-away view of a fourth irradiation apparatus in accordance with the prior art

A further attempt to provide production line sterilization is described in Swedish Patent Application 9602377-5 filed Jun. 14, 1996 which describes an apparatus for defocussing and bending an electron beam to provide simultaneous double-sided irradiation of a product stream. As shown in FIG. 4, in this device the main shield 15 encloses the radiation source and beam spreading system 16, while a product handling system 17 delivers product to the radiation source 16 by means of a tortuous path designed to block radiation leakage. Due to the limitations of the product handling system and the shielding disclosed in this patent, this device is limited to processing products which are thin and flexible.

SUMMARY OF THE INVENTION

The present invention serves to overcome the deficiencies identified in the prior art. It is therefore the primary object of the present invention to provide a compact irradiation apparatus integral to a production line that can sterilize product received from a manufacturing process on a continuous basis.

The above object is achieved by providing an irradiation apparatus for production line use comprising:
  (a) primary shield means for blocking radiation;
  (b) secondary shield means for blocking radiation;
  (c) an irradiation device; and
  (d) conveyor means;
  wherein said primary shield means further includes a central cavity therein and a channel extending therethrough which intersects the cavity and accommodates the conveyor means;

and wherein the secondary shield means comprises a plurality of discrete open containers, the containers having front and rear walls, the walls being substantially the size of the channel opening;

and wherein the primary and secondary shield means are of sufficient density to fully attenuate the radiation produced by the irradiation device;

and wherein the containers are integral to the conveyor means;

and wherein the irradiation device is disposed within the cavity to allow radiation of a product positioned in the containers as the containers pass through the cavity.

Preferably, the irradiation device is chosen from the group comprising electron accelerators, X-ray generators, and gamma-ray emitting radioisotopes.

More preferably, the conveyor means further includes a continuous track and drive means and the containers also integral to the conveyor means further include two pairs of wheels with each pair connected by an axle.

Conveniently, the continuous track is elliptical, the channel is substantially linear, and the front and rear walls are parallel.

More conveniently, the primary shield further includes tunnels co-linear with the conveyor means and extending from the channels, the walls of the tunnels progressively diminishing in thickness as the tunnels extends outward.

Even more conveniently, the continuous track is circular, the channel is semi-circular, the axles extending between the wheels of the containers are aligned radially inward, the front and rear walls of the containers are shaped to accommodate the semi-circular channel.

Even more preferably, the primary shield means is concrete or steel and the secondary shield means is taken from the group consisting of steel, lead, tungsten or uranium.

In an alternate embodiment, the invention comprises an irradiation apparatus for production line use comprising:
(a) primary shield means for blocking radiation;
(b) secondary shield means for blocking radiation;
(c) an irradiation device; and
(d) conveyor means;
wherein the primary shield means further includes a central cavity therein and a channel extending therethrough which intersects the cavity and accommodates the conveyor means;

and wherein the conveyor means comprises an auger and drive means, the diameter of the auger substantially equal to the channel opening;

and wherein the secondary shield means comprises the threaded portion of said auger;

and wherein the primary shield means and the thread portion of the auger is of sufficient density to fully attenuate the radiation produced by the irradiation device;

and wherein the irradiation device is disposed within the cavity to allow radiation of a product positioned between successive threads of the auger and in the cavity.

Preferably, the irradiation device is chosen from the group comprising electron accelerators, X-ray generators, and gamma-ray emitting radioisotopes.

Conveniently, the primary shield means is concrete or steel and the secondary shield means is taken from the group consisting of steel, lead, tungsten or uranium.

The advantages of the present invention are readily apparent. The sterilization apparatus is relatively small and compact, thereby allowing it to be placed into a production line where the product to be sterilized is manufactured. Further, by integrating a secondary shield in the form of a container into the conveyor system, continuous throughput of the product to be sterilized is provided at rates equal to the output of the product manufacturing operation. Product ready for sterilization is simply placed into a container and moved into the irradiation zone, with no additional product movement or shield manipulation required. The walls of the containers or the threads of the auger are of sufficient thickness and height, so that when used in conjunction with the primary shield means, they attenuate all the radiation generated by the irradiation device. As well, the overall amount of shielding is reduced, which in turn reduces the area required to house the irradiation apparatus.

BRIEF DESCRIPTION OF THE DRAWINGS

A better understanding of the invention will be obtained by considering the detailed description below, with reference to the following drawings in which.

DETAILED DESCRIPTION OF THE INVENTION

Figure 5:
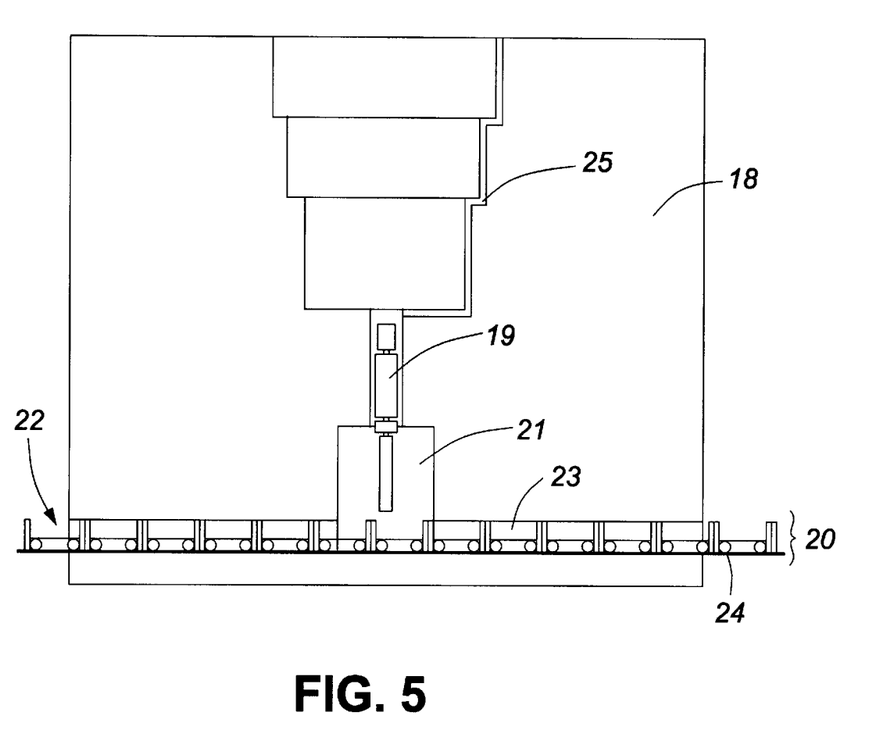
FIG. 5 is a side cut-away view of an irradiation apparatus in accordance with a first embodiment the present invention.
Figure 6:
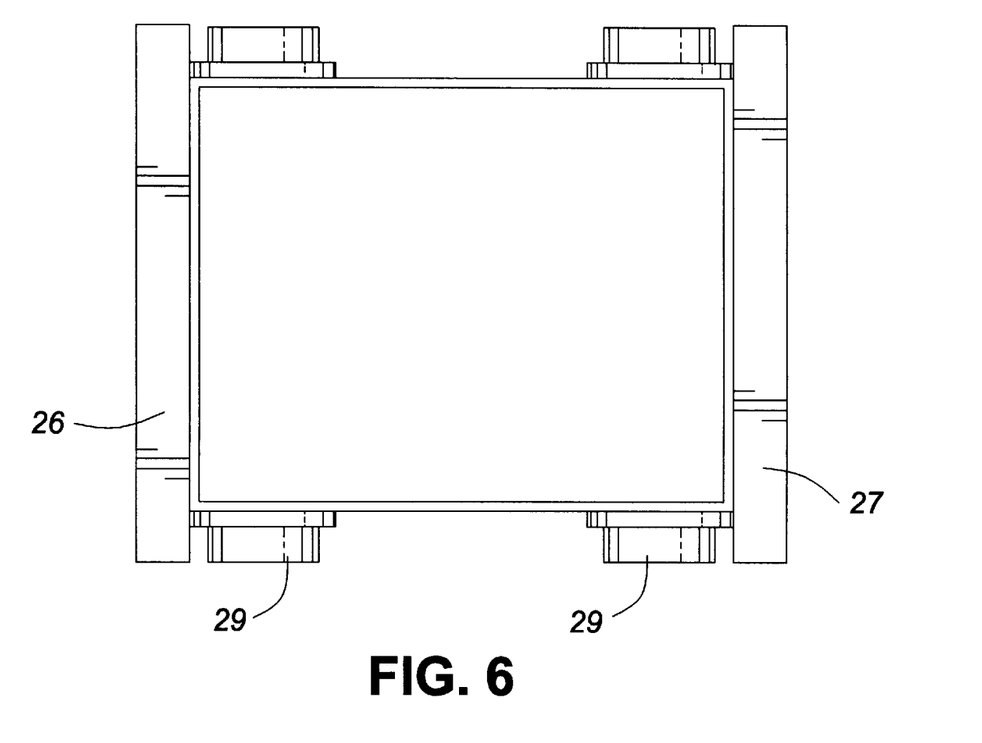
FIG. 6 is a top view of the product container integral to the conveyor system.
Figure 7:
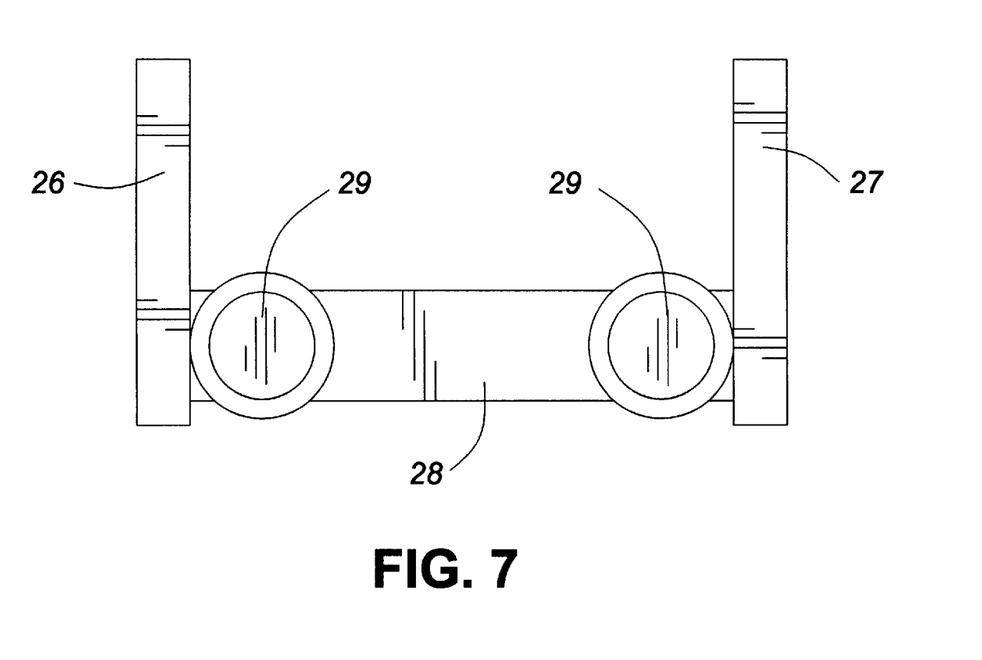
FIG. 7 is a side view of the product container integral to the conveyor system.

With reference to FIGS. 5, 6 and 7 a first embodiment of the present invention is disclosed. Referring to FIG. 5, the main components of the invention are depicted which include a primary shield 18, an irradiation device 19, and a conveyor system 20. The irradiation device extends into a cavity 21 formed in the primary shield 18, and the conveyor system 20 is positioned in a channel, shown generally as 22, which penetrates the primary shield 18. Integral to the conveyor system 20 are shielded containers 23 which ride on track 24 and a drive means (not shown) which propels the containers 23 around track 24.

The irradiation device 19 may either be an electron accelerator with energy exceeding 1 MeV, an electron accelerator with an x-ray converter, or a source of radioactive isotopes which may be Cobalt-60, Cesium-137 or some other source. In an embodiment where an isotope source is used it is required that the source be cooled and be provided with a fail safe shield so that the product transport mechanism can be safely removed for service if necessary. The primary shield 18 is constructed of concrete, steel or similarly dense material in the form of a poured slab, blocks or other suitable construction methodology which will ultimately result in a shield providing the required radiation attenuation. The minimum thickness of the primary shield 18 in all directions from the radiation treatment zone (except for the direction of the axis of the conveyor system 20) is sufficient to reduce the radiation level to a safe level for workers in the immediate area of the apparatus, based solely on the attenuation by the primary shielding 18. Passageways 25 allow for the removal of ozone and any gaseous products of radiolysis which may be created during the sterilization process.

Referring to FIGS. 6 and 7, the containers 23 integral to the conveyor system 20 are depicted. The containers comprise front walls 26, rear walls 27, a base 28 and wheels 29. Axles (not shown) extend between pairs of wheels 29. Front and rear walls 26, 27 provide a secondary level of shielding to prevent radiation from leaking along channel 22. This requires that the front and rear walls 26, 27 be substantially the same size as the opening of channel 22 and that they be constructed of a material such that they provide equal or more attenuation than the primary shield 18. Preferably, the front and rear walls 26, 27 will be constructed of steel, lead tungsten or uranium.

Figure 8:
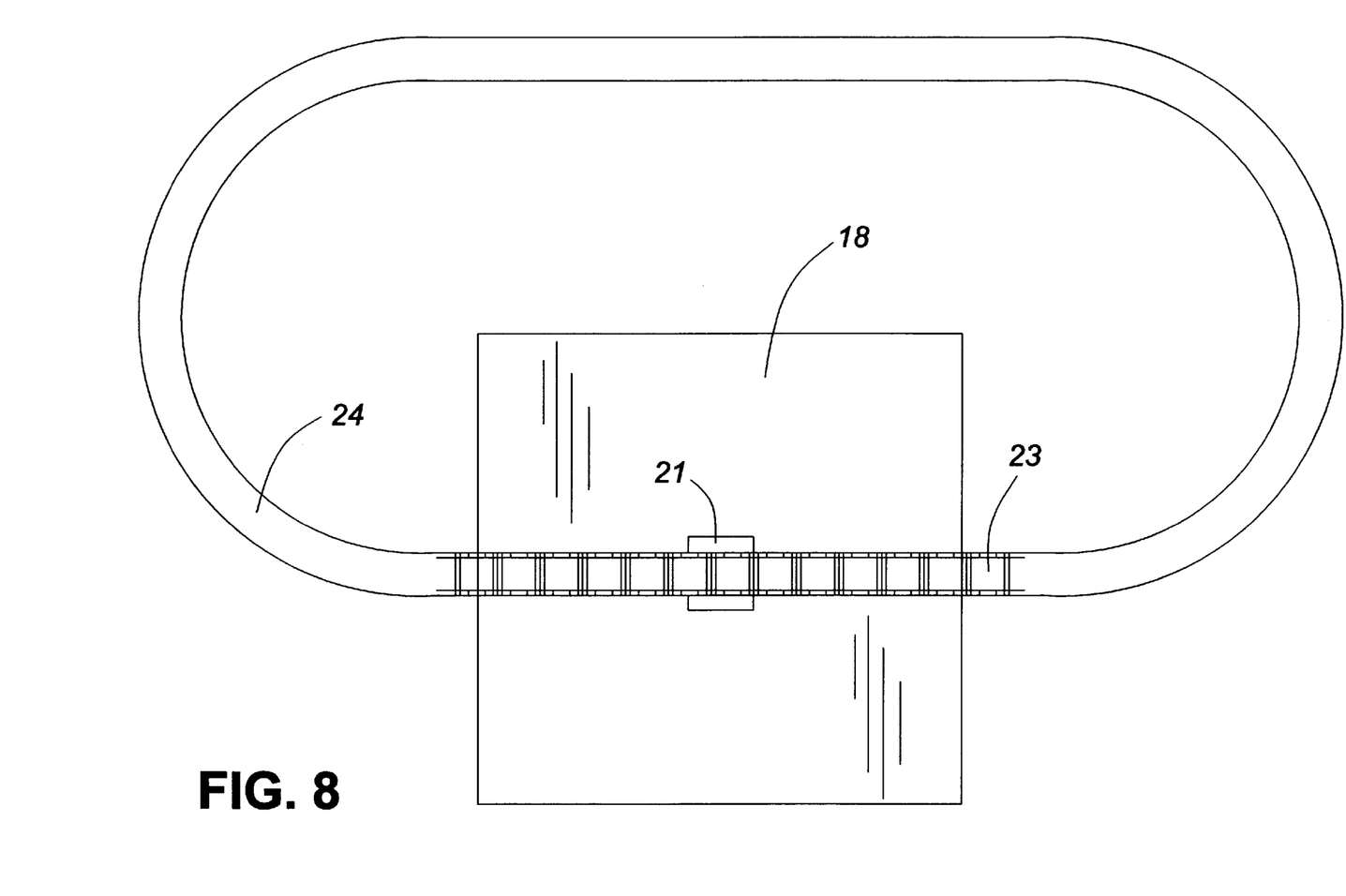
FIG. 8 is a top cut-away view of an elliptical configuration of the conveyor means.

Referring to FIG. 8, the layout of the conveyor system 20 is shown. As described earlier, the conveyor system 20 includes containers 23, a track 24 and drive means (not shown). The containers 23 are positioned end to end on track 24, with the track 24 being generally elliptical in shape. The elliptical shape ensures that the portion of track 24 extending through the primary shield 18 is generally linear. The number of containers 23 is chosen to maximize product throughput, while ensuring that there is sufficient high density material in channel 22 to fully attenuate the radiation in the processing zone that would otherwise escape through channel 22. Finally, the containers 23 integral to the conveyor system 20 may be driven in a variety of ways including mechanical, electrical or pneumatic drive systems.

In operation, the product to be sterilized is placed in container 23 and container 23 is moved into the irradiation zone directly below irradiation device 19. The product is then irradiated and the front and rear walls 26, 27 in conjunction with the primary shielding 18 attenuate any radiation present in cavity 21 or along channel 22. It will be understood by those skilled in the art that since, in practice, there will be some (albeit small) gap between the wall of channel 22 and the front or rear walls 26, 27 of container 23, the preferred embodiment may either incorporate a small amount of shielding outside the primary shield 18 placed perpendicular to and near the channel 22 opening, or a slightly curved channel 22, the extent of such curvature being limited to that which blocks direct radiation escape in a straight line path through the gap.

Figure 9:
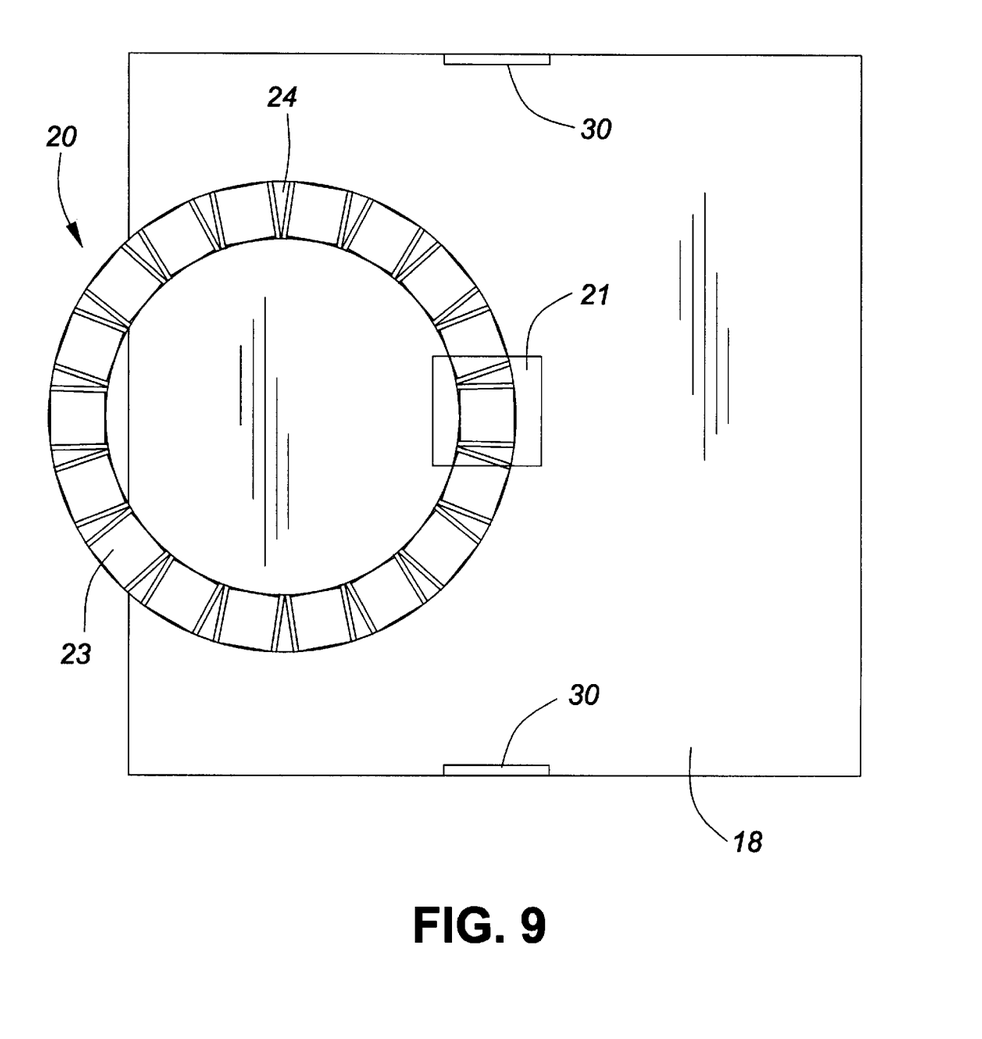
FIG. 9 is a top cut-away view of a circular configuration of the conveyor means.

Referring to FIG. 9, an alternatively configured conveyor system is depicted. In this embodiment, the conveyor system, shown generally as 20, is circular in shape and the containers 23 are rigidly linked in a circular array. In order to facilitate easy movement of the containers 23 along track 24, the axles connecting the wheels 29 point radially inward and the front and rear walls 26, 27 of containers 23 are shaped to follow the curved walls of semi-circular channel 22. Small supplementary high density shields 30 are added to the primary shield 18 to replace primary shield 18 lost near cavity 21 due to the space occupied by channel 22.

Figure 10:
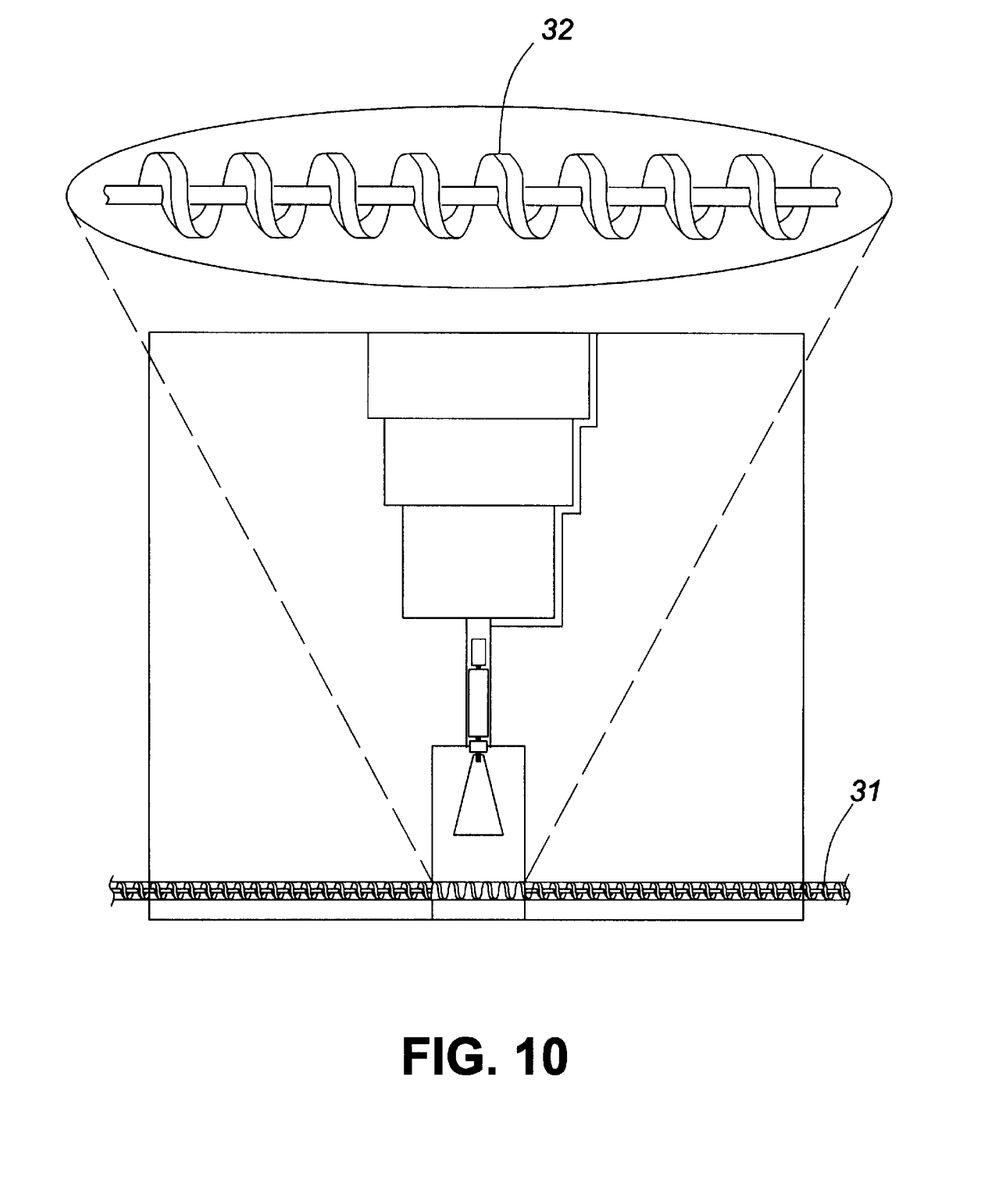
FIG. 10 is a side cut-away view of an irradiation apparatus in accordance with a second embodiment of the present invention.

FIG. 10 depicts yet another embodiment of the conveyer system of the present invention. The conveyer system comprises an auger 31 which combines the functions of product transport and secondary shielding. The threads 32 of the auger 31 provide the secondary shielding, the diameter of the auger 31 being substantially equal to the width of channel 22. Similar to the construction of front and rear walls 26, 27, the material of the auger 31 has sufficient density to attenuate any radiation attempting to escape down channel 22. The auger 31 has a solid core in all sections of the product transport system except for the portion immediately below the radiation device 19 where it will be of the open screw type, so as to eliminate shadowing of the radiation beam. The product to be sterilized is simply placed between adjacent threads 32 and the rotation of auger 31 moves the product to be sterilized into the irradiation zone.

Figure 11:
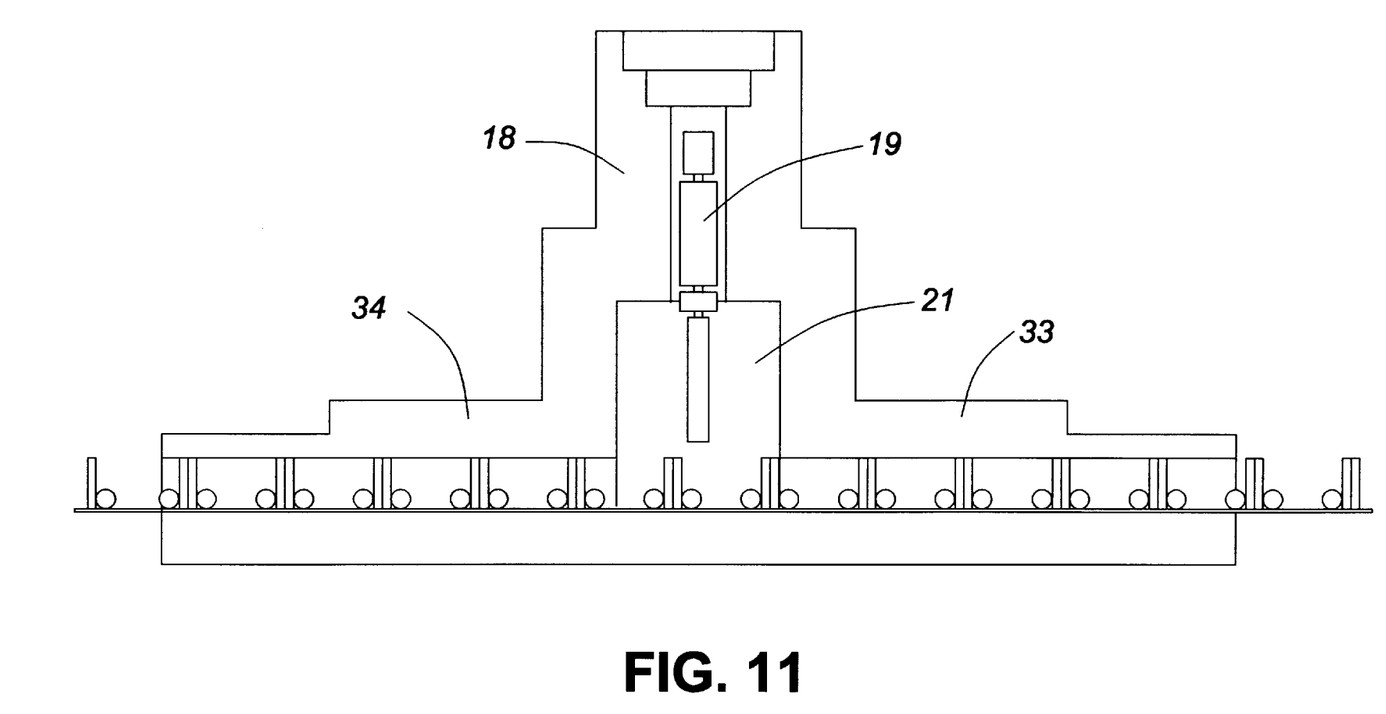
FIG. 11 is a side cut-away view of an irradiation device in accordance with a third embodiment of the present invention.

A final embodiment of the present invention is depicted in FIG. 11. This embodiment consists of a primary shield 18 as described in previous embodiments, but in this embodiment the density of the primary shield 18 is the same as that of the front and rear walls 26, 27 of containers 23. This serves to reduce the thickness of the principle shield surrounding the irradiation device 19 and the cavity 21. However, the reduction in the size of primary shield 18 necessitates the inclusion of an extension to the primary shield 18. Tunnels 33, 34 of progressively diminishing thickness extend outwardly from channel 22 over conveyor system 20. This ensures that any radiation scattered along the channel 22 is attenuated before reaching the production room floor.

A person understanding this invention may now conceive of alternative structures and embodiments or variations of the above all of which are intended to fall within the scope of the invention as defined in the claims that follow.

We claim:

1. An irradiation apparatus for production line use comprising:

(a) primary shield means for blocking radiation;

(b) secondary shield means for blocking radiation;

(c) an irradiation device; and (d) conveyor means;

wherein the primary shield means further includes a central cavity therein and a channel extending therethrough which intersects the cavity and accommodates the conveyor means;

and wherein the secondary shield means comprises a plurality of discrete open containers, the containers having front and rear walls, the walls being substantially the size of the channel opening;

and wherein the primary and secondary shield means are of sufficient density to fully attenuate the radiation produced by the irradiation device;

and wherein the containers are integral to the conveyor means;

and wherein the irradiation device is disposed within the cavity to allow radiation of a product positioned in the containers as the containers pass through the cavity.

2. The apparatus of claim 1 wherein the irradiation device is chosen from the group comprising electron accelerators, X-ray generators, and gamma-ray emitting radioisotopes.

3. The apparatus of claim 2 wherein the conveyor means further includes a continuous track and drive means and the containers also integral to the conveyor means further include two pairs of wheels with each pair connected by an axle.

4. The apparatus of claim 3 wherein the continuous track is elliptical, the channel is substantially linear, and the front and rear walls are parallel.

5. The apparatus of claim 4 wherein the primary shield further includes tunnels co-linear with the conveyor means and extending from the channels, the walls of the tunnels progressively diminishing in thickness as the tunnels extends outward.

6. The apparatus of claim 3 wherein the continuous track is circular, the channel is semicircular, the axles extending between the wheels of the containers are aligned radially inward, and the front and rear walls of the containers are shaped to accommodate the semi-circular channel.

7. The apparatus of claim 4, 5 or 6 wherein the primary shield means is concrete or steel and the secondary shield means is taken from the group consisting of steel, lead, tungsten or uranium.

8. An irradiation apparatus for production line use comprising:

(a) primary shield means for blocking radiation;

(b) secondary shield means for blocking radiation;

(c) an irradiation device; and (d) conveyor means;

wherein the primary shield means further includes a central cavity therein and a channel extending therethrough which intersects the cavity and accommodates the conveyor means;

and wherein the conveyor means comprises an auger and drive means, the diameter of the auger substantially equal to the channel opening;

and wherein the secondary shield means comprises the threaded portion of the auger;

and wherein the primary and secondary shield means are of sufficient density to fully attenuate the radiation produced by the irradiation device;

and wherein the irradiation device is disposed within the cavity to allow radiation of a product positioned between successive threads of the auger and in the cavity.

9. The apparatus of claim 8 wherein the irradiation device is chosen from the group comprising electron accelerators, X-ray generators, and gamma-ray emitting radioisotopes.

10. The apparatus as claimed in claim 9 wherein the primary shield means is concrete or steel and the secondary shield means is taken from the group consisting of steel, lead, tungsten or uranium.

* * * * *